(12) United States Patent
Baist et al.

(10) Patent No.: US 6,243,162 B1
(45) Date of Patent: Jun. 5, 2001

(54) SYSTEM FOR OPTICALLY EXAMINING PLASTIC CARD SURFACES

(75) Inventors: Bernhard Baist, Wuppertal; Alexander Melzer, Ennepetal, both of (DE)

(73) Assignee: Melzer Maschinenbau GmbH, Schwelm (DE)

( * ) Notice: Subject to any disclaimer, the term of this patent is extended or adjusted under 35 U.S.C. 154(b) by 0 days.

(21) Appl. No.: 09/297,779

(22) PCT Filed: Sep. 4, 1998

(86) PCT No.: PCT/EP98/05608

§ 371 Date: Jul. 16, 1999

§ 102(e) Date: Jul. 16, 1999

(87) PCT Pub. No.: WO99/13321

PCT Pub. Date: Mar. 18, 1999

(30) Foreign Application Priority Data

Sep. 9, 1997 (DE) ............................................. 197 39 328

(51) Int. Cl.⁷ .................................................... G01N 21/00
(52) U.S. Cl. ............................................................. 356/237.1
(58) Field of Search ............................... 356/237.1, 237.2, 356/71

(56) References Cited

U.S. PATENT DOCUMENTS

| 4,202,626 | * | 5/1980 | Mayer, Jr. et al. | 355/52 |
| 4,501,439 | * | 2/1985 | Antes | 283/91 |
| 5,155,558 | | 10/1992 | Tannenbaum et al. | 356/446 |
| 5,436,716 | * | 7/1995 | Stein | 356/71 |
| 5,640,237 | | 6/1997 | Esrig et al. | 356/237 |

FOREIGN PATENT DOCUMENTS

| 0 735 361A2 | * | 2/1996 | (EP) | G01N/21/88 |
| 0 735 361 | | 10/1996 | (EP) | G01N/21/88 |

\* cited by examiner

Primary Examiner—Frank G. Font
Assistant Examiner—Phi Natividad
(74) Attorney, Agent, or Firm—Townsend and Townsend and Crew, LLP

(57) ABSTRACT

In the optical examination of plastic cards, the latter are illuminated with focused light, which is mixed with a diffuse component, in order reliably to discriminate even relatively slight differences in the reflectivity of the surface sections.

19 Claims, 2 Drawing Sheets

SYSTEM FOR OPTICALLY EXAMINING PLASTIC CARD SURFACES

Figure 1:
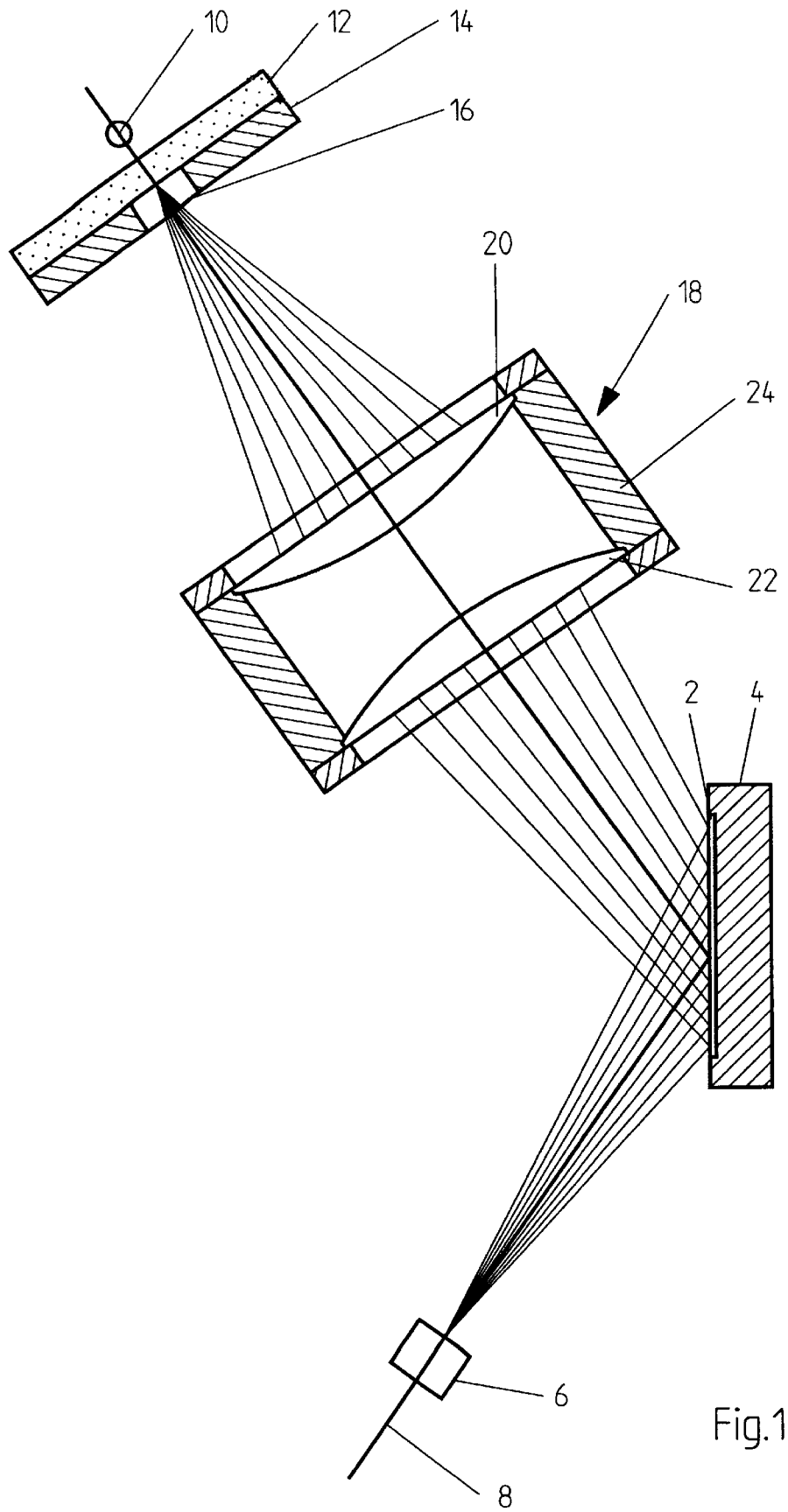

The invention relates to a method for examining plastic cards having the features named in the preamble of claim 1. The invention can also be applied in the case of other flat objects in which detection of surface defects is to be undertaken.

In the fabrication of plastic cards such as identity cards, chip cards, credit cards and the like, stringent requirements are placed on maintaining narrow quality tolerances. Thus, in particular, the surfaces are to be free from scratches; for example, signature strips envisaged may not be lacking or be impressed askew or otherwise be defective, impressed holograms must be free from defects and be positioned at the correct point, etc. Known methods use a video camera with downstream image processing for monitoring the surface, a specimen under examination being illuminated with diffuse light so that the card surfaces can be effectively detected. An operator is then responsible for fixing the limits between "free from defects" (good) and "defective" (rejects).

The cards under discussion here frequently consist of a plurality of layers which are laminated together and of which at least one is generally printed. A desired alignment and quality of the overprinted image is naturally a part of the surface examination. Consequently, the cards are illuminated during examination with diffuse light such that the video camera picks up an image reflected from the surface of the specimen under examination. Such an optical examining method is certainly largely insensitive with respect to slight sagging of the flat specimens under examination, but it has the great disadvantage that scratches and grooves are imaged only with poor contrast.

It is therefore the object of the invention to develop a method according to the preamble of claim 1 in such a way that even relatively slight surface defects can be detected and the examination cannot be falsified by overprinted images.

This object is achieved by means of the features of patent claim 1. Claims 5 and 7 name important applications of the method. Claims 8 to 17 relate to an illuminating device with which the method according to the invention can be carried out.

The result is to create a method which by reflection supplies a light/dark image of a card surface with an adequate contrast for simultaneously detecting a glossy card surface and an intentional two-dimensional change, achieved by embossing, in the card surface such as, for example, a hologram, signature field, etc. In addition to surface defects such as scratches and grooves, it is, in particular, the contours and thus the position of the intentional two-dimensional changes in the card surface which can be reliably detected. A further substantial advantage consists in that, to mirror the card surface, the position of the latter relative to the beam path is no longer quite so critical, with the result that even should the card possibly sag the reflection is still sufficiently good. The diffuse light component supplies a scattered reflection component which leads to a lesser situational sensitivity of the reflection. The loss in contrast occurring to this extent is slight. The viewing possibilities are consequently substantially enhanced according to the invention.

Further embodiments and advantages of the invention are to be gathered from the dependent claims and the following description.

Figure 2:
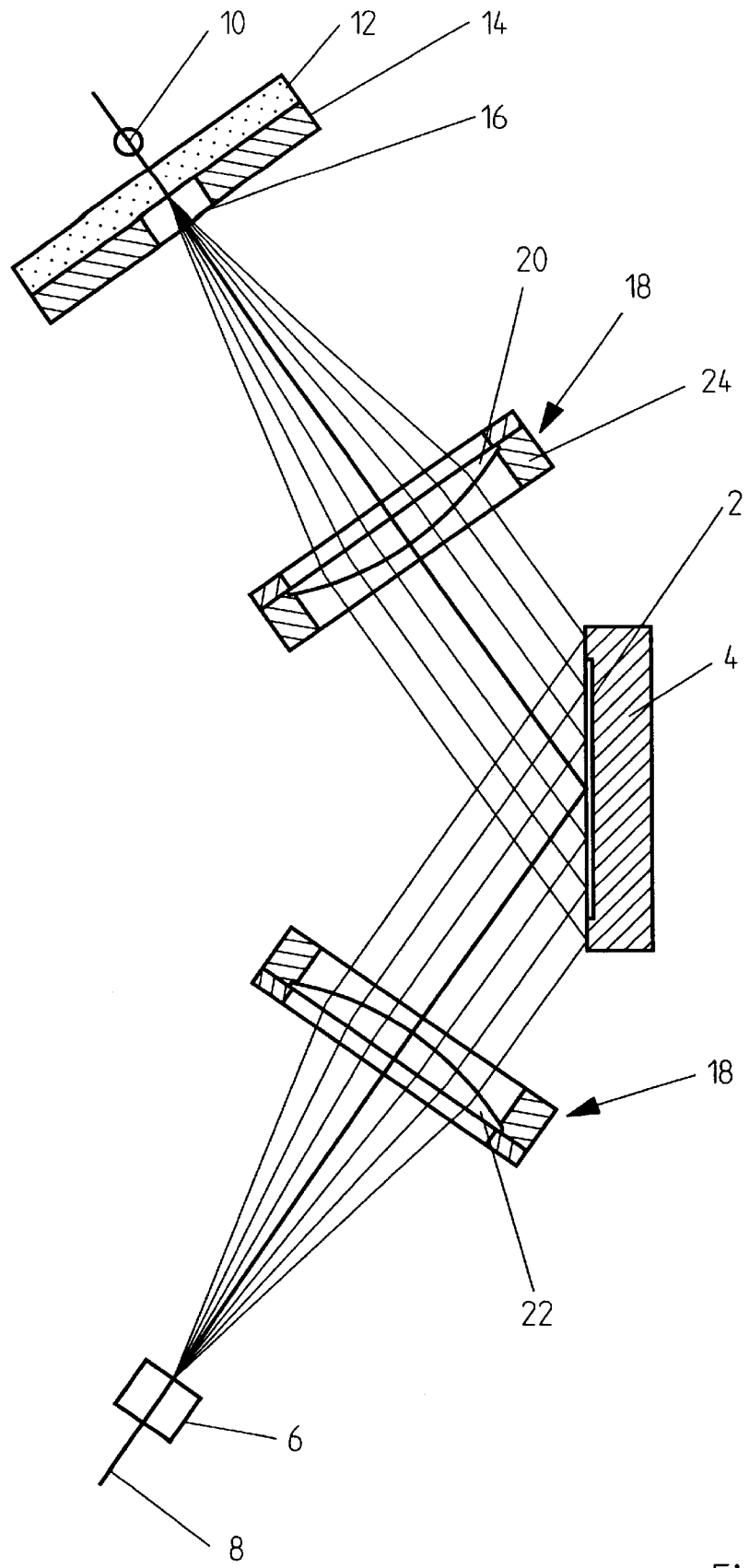

The invention is explained in more detail below with the aid of the exemplary embodiments represented in the attached drawings, in which:

FIG. 1 shows a diagram of a first exemplary embodiment of an illuminating device in combination with a video camera, and FIG. 2 shows a diagram of a second exemplary embodiment of an illuminating device in combination with a video camera.

In accordance with FIG. 1, plastic cards to be examined are conveyed as specimens under examination 2 along a carrier for specimens under examination, here a channel 4, which runs perpendicular to the plane of the drawing. A video camera, of which only the entrance aperture 6 is indicated, "sees" the specimens to be examined 2 at an angle of its optical axis 8 of, for example, 30°. The illuminating device comprises a light source 10, which corresponds approximately to a point light source and illuminates a diffuser 12. The diffuser 12, is, for example, a slab made from milk glass or a plastic with appropriate opacity. The diffuser is fixed on a plate 14 which is provided with a bore 16. The bore 16 forms an aperture for the exit of light. Provided between this aperture and the specimens under examination 2 is a lens arrangement 18 comprising two plano-convex lenses 20, 22 whose plane sides point outward, and which are accommodated in a common housing 24. The lens arrangement focuses the light from the aperture bore 16 onto the respective specimen under examination. Alternatively, it is also possible to use Fresnel lenses. However, in addition to a directed radiation the light also contains a diffuse component, and it has proved that, with the aid of such an illumination, surfaces on the specimens under examination in the case of which the reflectivity on the surfaces exhibits only relatively slight differences are also differently imaged with good contrast. This holds, in particular, for signature strips which—given the same color as the card—are somewhat rougher than the surface of the card itself. Such strips appear dark against a bright background in the image. An impressed hologram, by contrast, appears bright before a dark background, a prismatic structure present in the case of a hologram also supplying image information in this case.

The size of the bore 16, which represents an aperture, and the diffusing action of the slab 12 can be optimized by means of a few experiments in order to set the diffuse component of the light.

All the elements are arranged on a common optical axis 8 which, in the case of arrangement in the beam path, forms with the plane of the surface, which is to be examined, of a specimen under examination 2 an angle differing from 0° and 90°; the angle is preferably between 30° and 60°.

Whereas in the exemplary embodiment in accordance with FIG. 1 a converging beam falls onto the specimens to be examined 2, in accordance with a second exemplary embodiment, in accordance with FIG. 2, the specimens under examination can be arranged in a parallel beam path. For this purpose, the positive lens system 18 comprises two separately arranged positive lenses 20, 22, which can be the same type of lenses as described with reference to FIG. 1, except that they are spatially separated and the carrier 4 for the specimens to be examined 2 is arranged between them. Otherwise, the statements relating to the first exemplary embodiment in accordance with FIG. 1 are valid correspondingly for the second exemplary embodiment in accordance with FIG. 2.

In accordance with a method according to the invention for optically examining plastic card surfaces, in which method at least a subregion of a surface of the specimens under examination 2 is illuminated and an image thereof taken with a video camera is compared with a stored pattern, it is therefore provided that the specimens under examination 2 are illuminated with light which is reflected in a focused fashion into the video camera and which is directionally incident radiation containing a diffuse component, with the result that the surface is reflected. This produces a contrast image of the surface in the bright-dark region as a function of the nature of the surface and its desired (such as embossed images) or unwanted (such as scratches, grooves, etc.) roughnesses. In this case, the diffuse component of the light can be set via the size of an aperture of the directionally incident radiation. The specimens under examination 2 can be illuminated by parallel beams of the directionally incident radiation. Alternatively, the specimens under examination 2 can be illuminated by converging beams of the directionally incident radiation.

What is claimed is:

1. A method for optically examining plastic card surfaces, said method comprising:

illuminating at least a subregion of a surface to be examined with directionally incident radiation containing a diffuse component, wherein said radiation is reflected;

adjusting the surface to focus substantially all reflected light into a video camera to produce an image of the surface; and comparing the produced image with stored images.

2. The method as claimed in claim 1, wherein the diffuse component of the light is set via the size of an aperture for the directionally incident radiation.

3. The method as claimed in claim 1 or 2, wherein the surface under examination is illuminated by parallel beams of the directionally incident radiation.

4. The method as claimed in claim 1 or 2, wherein the surface under examination is illuminated by converging beams of the directionally incident radiation.

5. The method as claimed in claim 1 or 2, for examining cards onto which at least one object is impressed.

6. The method as claimed in claim 5, wherein the object is formed by a hologram.

7. The method as claimed in claim 5, wherein a signature strip is impressed onto the cards.

8. An illuminating device for optically examining plastic card surfaces, said device comprising a light source element (10), a diffuser element (12) arranged downstream of the light source element (10), an aperture element (16) arranged upstream or downstream of the diffuser element (12) and a positive lens system (20, 22) arranged downstream of the aperture element (16) for focusing substantially all of the light downstream of a beam path into a detecting device (6), all elements being arranged on a common optical axis (8) which, together with the plane of a surface of a plastic card (2) which is to be examined, forms an angle in a range from 0° and 90° when arranged in the beam path.

9. The device as claimed in claim 8, wherein the light source element (10) comprises a point of light source.

10. The device as claimed in claim 8 or 9, wherein the diffuser element (12) is formed by a slab, arranged perpendicular to the optical axis (8), with the character of milk glass.

11. The device as claimed in claim 8 or 9, wherein the aperture (16) is formed by a hole in a plate (14) arranged perpendicular to the optical axis (8).

12. The device as claimed in claim 10, wherein a slab is fastened on and/or under the plate (14).

13. The device as claimed in claim 8, wherein the positive lens system (18) comprises two plano-convex (20, 22) lenses.

14. The device as claimed in claim 8, wherein the optical axis (8) forms an angle of between 30° and 60° with the plane of a surface of the plastic card (2).

15. The device as claimed in claim 14 with a video camera as is detecting device (6), wherein the optical axis thereof forms with the plane of a surface of the plastic card (2) an angle which is approximately equal in a mirror-image fashion to that of the optical axis (8) of the illuminating device.

16. The device as claimed in claim 8, wherein the plane of a surface of the plastic card (2) is arrange din a beam section between two positive lenses (20, 22) forming a positive lens system (18), a parallel beam path being constructed in the beam section.

17. The device as claimed in claim 8, wherein the plane of a surface of the plastic card (2) is arranged in a beam section downstream of the positive lens system (18), a converging beam output being constructed in the beam section.

18. A method for optically examining a plurality of plastic cards in sequence, each plastic card having a surface, said method comprising:

illuminating at least a subregion of the surface of each of the plurality of plastic cards to be examined with directionally incident radiation containing a diffuse component, wherein said radiation is reflected;

adjusting the surface to focus substantially all reflected light into a video camera to produce an image of the surface; and comparing the produced image of each of the plurality of plastic cards with stored images.

19. The method of claim 18, wherein each of the plurality of plastic cards are advanced into a position where the subregion of the surface of each of the plurality of plastic cards is illuminated by a conveyor assembly.

* * * * *